United States Patent
Noyer et al.

[11] Patent Number: 6,056,779
[45] Date of Patent: May 2, 2000

[54] PROSTHESIS FOR THE KNEE ARTICULATION

[75] Inventors: Daniel Noyer, Maubec; Marc Augoyard, Tassin la Demi Lune; Pierre Roussouly, Saint Cyr au Mont d'or; Christophe Roy, Lyons, all of France

[73] Assignee: Societe Ortho-Id, France

[21] Appl. No.: 09/111,520

[22] Filed: Jul. 8, 1998

[30] Foreign Application Priority Data

Jul. 10, 1997 [EP] European Pat. Off. ............ 97440060

[51] Int. Cl.[7] ........................................ A61F 2/38
[52] U.S. Cl. ................................. 623/20; 623/18
[58] Field of Search ............................. 623/20, 18

[56] References Cited

U.S. PATENT DOCUMENTS 4,808,185  2/1989  Peneberg et al. ..................... 623/20
5,137,536  8/1992  Koshino ............................ 623/18 X
5,219,362  6/1993  Tuke et al. .......................... 623/20

FOREIGN PATENT DOCUMENTS 3314038 of 1983 Germany.

*Primary Examiner*—Michael J. Milano
*Assistant Examiner*—Brian Pellegrino
*Attorney, Agent, or Firm*—Ostrolenk, Faber, Gerb & Soffen, LLP

[57] ABSTRACT

A prosthesis for the knee articulation is provided which has a femoral implant having two condyles which are of convex shape, each having a variable radius, and a tibial implant having two cavities, each of which interacts with a respective one of the condyles. In its posterior region, the internal condyle has a spherical prominence which projects from the contact plane of the internal condyle and is intended to interact with a spherical cap hollowed into the posterior region of the internal cavity of the tibial implant.

4 Claims, 1 Drawing Sheet

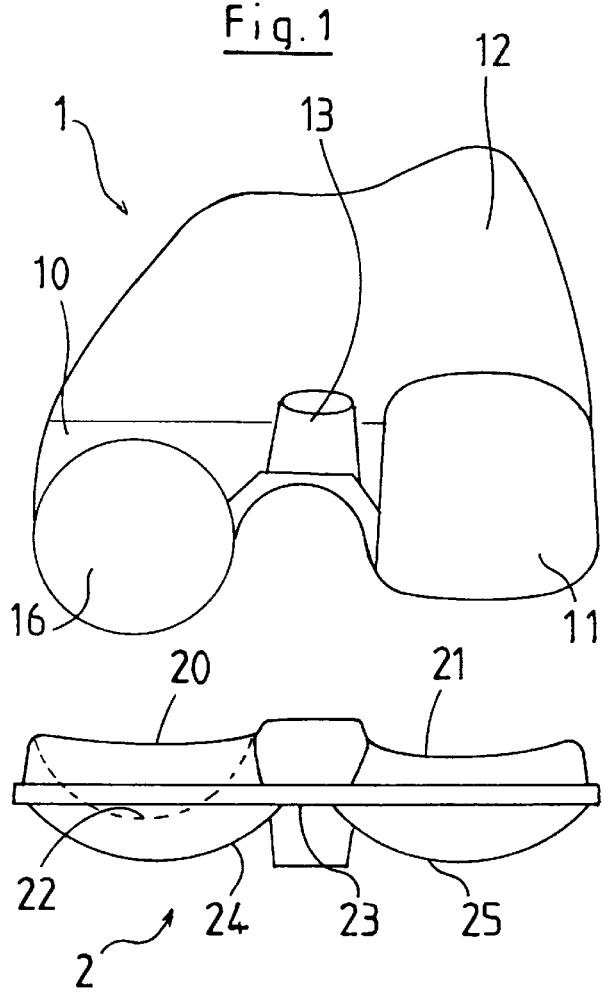
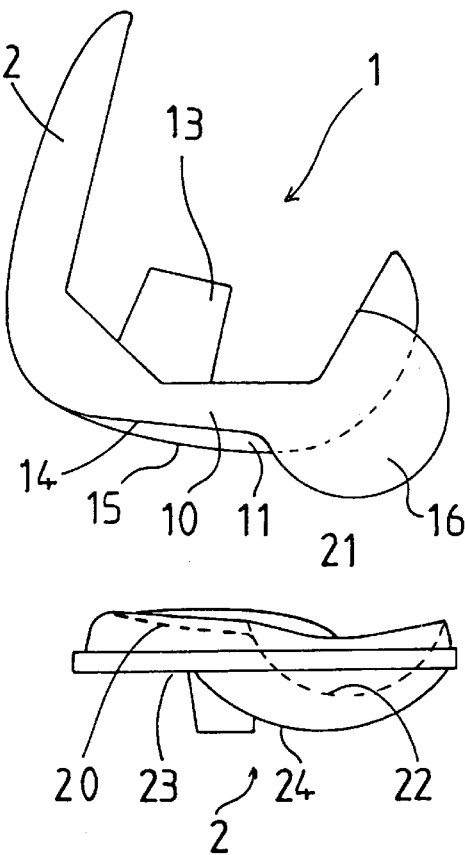
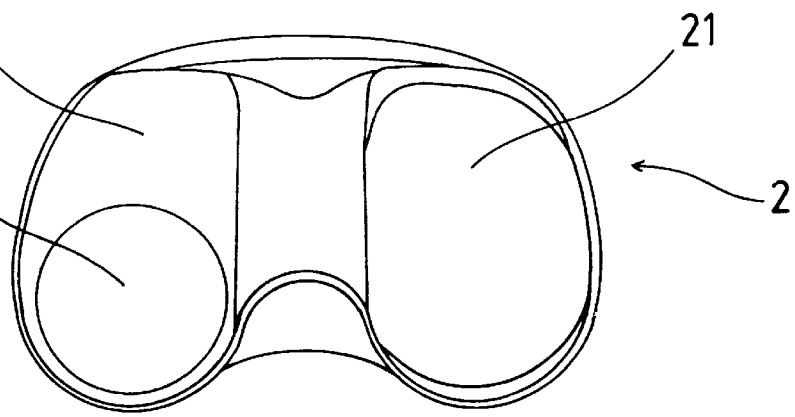

PROSTHESIS FOR THE KNEE ARTICULATION

BACKGROUND OF THE INVENTION

1. Field of the Invention

The present invention relates to a prosthesis for the knee articulation.

2. Description of the Related Art

The articulation of the knee allows the leg to move in flexion and extension on the thigh, and is formed between the femur and the tibia, on the one hand by means of their ends, namely respectively the femoral condyles and the tibial plateau, and on the other hand by means of the patella and the femoral trochlea, and ligaments which prevent possible dislocation.

During flexion, the condyles, which are of convex shape, roll and glide over the tibial plateau to allow a degree of flexion which is extensive but nevertheless limited by the soft matter.

Further, flexion is accompanied by axial rotation of the tibia relative to the femur.

In hyperextension, the femur and the tibia are locked in continuation of one another, which makes it possible to maintain posture without fatigue since no muscular effort is necessary.

In the event of an articular injury to the knee, it is sometimes necessary to resort to the fitting of a partial or total prosthetic knee articulation.

The first prostheses for the knee articulation were simple hinges, permitting only a flexion/extension movement by pivoting about a transverse axis, which presented the drawbacks of, on the one hand, an unnatural walking action because the axial pivoting of the tibia relative to the femur is not reproduced, and on the other hand, the fact that complete flexion is not possible.

Most of the knee prostheses known at present include a femoral implant which comprises two condyles and a trochlear shield, the latter being intended to interact with a prosthetic or natural patella, while the two condyles articulate with a tibial implant which includes a plateau covered by a mobile or immobile meniscal element, generally made of polyethylene.

These prostheses are referred to as gliding prostheses, and reproduce the movement of the natural articulation by combining the rolling and gliding of the condyles over the meniscal element.

All of these prostheses have the same drawback, namely a relatively short average life, of the order of ten years, because of the wear to the meniscal element.

The explanation for this is that most existing prostheses include two condyles which are of convex shape and have a radius that is not constant, and a meniscal element which has two concave cavities, also with a radius that is not constant. The contact between the condyles and the meniscal element then takes place linearly, so that during the gliding movement, a phenomenon by which the surfaces of said cavities are abraded takes place over the long term.

In order to lengthen the life of prostheses, some have proposed to distribute the wear phenomenon by creating a second contact surface, through possible gliding of the meniscal element over the tibial plateau.

Others have proposed to separate the twofold movement of gliding and rolling, the gliding taking place between the meniscal element and the tibial plateau and the rolling between said meniscal element and the condyles, the latter having a shape which is at least partially spherical, thus making it possible to obtain partial or total congruence.

However, these prostheses still have drawbacks, in particular in that they are of complex design. Specifically, they involve a large number of parts, which increases the risk of malfunction and requires perfect adjustment, lengthening the operating time to the detriment of the patient.

Prostheses are also known in which the gliding and rolling movements are separated and are respectively fulfilled by the internal condyle and the external condyle. This is the case of the prostheses described in documents U.S. Pat. No. 5,219,362 and German document DE 33 14 038, for each of which the internal condyle is partially spherical and congruent with the meniscal element, while the external condyle can roll over the implant. These prostheses do not allow complete reproduction of the natural movement of the knee articulation, in particular during complete flexion, because the internal and external condyles pivot about the same axis, which furthermore has an effect on the wear to the meniscal element.

If the ligaments are excessively loose, or if the cruciate ligaments are absent, in particular the posterior cruciate ligament, it is necessary to fit a so-called stabilized prosthesis, which is more complex than other prostheses.

Further to the characteristics described above, a stabilized prosthesis generally includes either a centering unit, which may or may not be provided with a spherical head, projecting centrally from the tibial plane and interacting with the femoral implant while passing through the intercondylar notch, or a hook-shaped part against which a transverse bar abuts during flexion, this bar extending through the intercondylar notch and joining the posterior parts of the condyles, or a unit which is arranged in the anterior central region of the tibial plateau and on which the base of the tracheal shield abuts in a hyperextension position.

Further to the complexity of the prosthesis, and the complexity of fitting it, there are still drawbacks of the limitation of the flexion, and above all the risks of detachment of the femoral and/or tibial implant due to repeated shocks when the various moving elements abut against a fixed element.

It will be noted that the prostheses described in the documents mentioned above do not permit perfect stability if some or all of the ligaments are absent, this being especially true of the one in prosthesis described in U.S. Pat. No. 5,219,362 in which the contact surfaces of the condyles are on the same level.

SUMMARY OF THE INVENTION

The object of the present invention is to overcome these various drawbacks by providing a prosthesis for the knee articulation which is of simple design, reproduces the movement of the natural articulation, has a longer life than existing prostheses, can be used if some or all of the cruciate ligaments are absent, is easier to fit and functions in a manner closely resembling the physiological movement of the knee.

The prosthesis for the knee articulation to which the present invention relates comprises a femoral implant having two condyles, an internal one and an external one, which are of convex shape with a radius that is not constant, and a tibial implant which has two cavities, an internal one and an external one, each of which interacts with one of said condyles, and is essentially a prosthesis wherein, in its posterior region, the internal condyle has a spherical prominence which projects from the contact plane of the internal condyle and is intended to interact with a spherical cap hollowed into the posterior region of the internal cavity of the tibial implant.

In hyperextension, the condyles rest on the tibial plateau, the internal condyle resting both via its median part and via its spherical posterior part engaged in the cap.

At the end of extension, in upright posture, and at the start of flexion, the load is transferred, as in the case of the natural articulation, onto the internal condyle so that the force is principally supported by the congruent spherical parts, where it is therefore distributed regularly, thus limiting the wear phenomenon.

When changing to flexion, the contact between the internal condyle and the tibial plateau is formed principally by the spherical parts, so that no rolling takes place, but merely gliding, which limits wear.

Further, the spherical parts allow the tibia to pivot in the axial sense, in addition to flexing, while the external condyle rolls and glides over the plateau, which makes it possible to reproduce the natural movement.

It will be noted that, during the flexion movement, whether when changing from extension to flexion or vice versa, the force is principally supported by the internal condyle, so that during the twofold movement of gliding and rolling by the external condyle, the wear to the material is minimized.

Further, the flexion can be performed in full, limited merely by the soft matter.

If the cruciate ligaments are absent, whether in flexion or extension, the prosthesis is sterilized because of the congruence of the spherical parts, which excludes sliding phenomena.

According to an additional feature of the prosthesis according to the invention, the spherical prominence is notched internally level with the intercondylar notch, in continuation of the groove for the patella to pass over the trochlear shield.

According to another additional feature of the prosthesis according to the invention, the face by which the tibial implant is coupled to the tibia includes a plane part from which two identical spherical caps project.

Further to the joining of a hole in order to insert a pin, the fitting of the tibial implant requires only plane resection and the production of two spherical cavities by means of a spherical cutter, which simplifies the intervention by the surgeon.

BRIEF DESCRIPTION OF THE DRAWINGS

FIG. 1 represents an exploded profile view of a prosthesis according to the invention.

FIG. 2 is a rear view of the prosthesis in FIG. 1.

FIG. 3 is a plan view of the tibial implant of the prosthesis in FIG. 1.

DETAILED DESCRIPTION OF THE INVENTION

The advantages and the characteristics of the device according to the invention will emerge more clearly from the following description, which relates to the drawings that represent nonlimiting embodiments of it.

Referring to FIGS. 1 and 2, it can be seen that a prosthesis according to the present invention comprises a femoral implant 1 and tibial implant 2.

The femoral implant 1 includes two condyles, an internal condyle 10 and an external condyle 11, a trochlear shield 12 and a unit 13 for securing a fastening means such as a pin (not shown), while as can also be seen in FIG. 3, the tibial implant includes two cavities 20 and 21 for supporting the respective contact faces 14 and 15 of the respective condyles 10 and 11.

In its posterior region, the internal condyle 10 includes a spherical prominence 16 extending beyond the bearing face 14, while the tibial implant includes, hollowed into the posterior region of the cavity 20, a spherical cap 22 intended congruently to receive a part of the spherical prominence 16.

In order to guarantee a substantially constant thickness of the tibial plateau 2 level with the spherical cap 22, without needing to increase the actual thickness of the tibial plateau 2, the lower face 23 of the latter, which is of plane general shape, is curved and forms a convex spherical cap 24. This spherical cap 24 is reproduced in mirror image by a convex spherical cap 25 level with the posterior region of the cavity 21.

The spherical caps 24 and 25 permit better distribution of loads during walking than the conventional prostheses whose tibial implant includes a flat lower face.

Further, the spherical caps 24 and 25 make it possible to avoid shearing, so that this allows the tibial implant to be cemented with a short pin, or even without a pin.

When fitting the tibial implant 2, after plane resection of the osseous material, a template and a spherical cutter are used to make two cavities in the form of a spherical cap, these being intended to accommodate the spherical caps 24 and 25, which simplifies the invention.

What is claimed is:

1. A prosthesis for the knee articulation, comprising:

a femoral implant having an internal condyle of convex shape and an external condyle of convex shape, the internal condyle and the external condyle each having a variable radius, a posterior region of the internal condyle having a spherical prominence projecting from a contact plane; and a tibial implant having an internal cavity and an external cavity, each of the internal and external cavities interacts with a respective one of the internal and external condyles, the spherical prominence on the internal condyle interacting with a spherical cap hollowed into a posterior region of the internal cavity in the tibial implant.

2. The prosthesis as claimed in claim 1, wherein the femoral implant further comprises a trochlear shield, and wherein the spherical prominence is notched to be internally level with an intercondylar notch in the tibial implant, continuing a groove for the patella to pass over the trochlear shield.

3. The prosthesis as claimed in claim 1, wherein the tibial implant further comprises a face, the face including a plane part having two identical projecting spherical caps, the tibial implant being coupled to the tibia at the face, the two spherical caps being implanted in two corresponding spherical cavities made in the osseous material.

4. The prosthesis as claimed in claim 2, wherein the tibial implant further comprises a face, the face including a plane part having two identical projecting spherical caps, the tibial implant being coupled to the tibia at the face, the two spherical caps being implanted in two corresponding spherical cavities made in the osseous material.

* * * * *